United States Patent [19]

Isaacson

[11] 4,277,706
[45] Jul. 7, 1981

[54] ACTUATOR FOR HEART PUMP

[75] Inventor: Milton S. Isaacson, Dayton, Ohio

[73] Assignee: Nu-Tech Industries, Inc., Dayton, Ohio

[21] Appl. No.: 30,280

[22] Filed: Apr. 16, 1979

[51] Int. Cl.³ .............................................. H02K 7/06
[52] U.S. Cl. ....................................... 310/80; 310/83; 128/1 D; 74/57
[58] Field of Search .................. 128/1 D; 310/80, 83, 310/17; 74/57

[56] References Cited

U.S. PATENT DOCUMENTS

| | | | |
|---|---|---|---|
| 2,956,188 | 10/1960 | White | 310/83 X |
| 2,978,621 | 4/1961 | Martinek | 310/83 X |
| 3,159,758 | 12/1964 | Hemperly, Jr. et al. | 310/83 |
| 3,278,774 | 10/1966 | Roller et al. | 310/80 |
| 3,402,308 | 9/1968 | Henschke | 310/80 |
| 3,433,983 | 3/1969 | Keistman et al. | 310/17 X |
| 3,515,966 | 6/1970 | De Valroger et al. | 310/17 |
| 3,548,227 | 12/1970 | Woodward | 310/83 |
| 3,660,704 | 5/1972 | Perkins | 310/80 |
| 3,829,726 | 8/1974 | Nilsson | 310/83 |
| 4,198,872 | 4/1980 | Metz | 74/57 |

OTHER PUBLICATIONS

"Energy Transmission Through Intact Skin", Newgard et al., 12/72, pp. 71-90.

Primary Examiner—Donovan F. Duggan
Attorney, Agent, or Firm—Wood, Herron & Evans

[57] ABSTRACT

A heart pump consisting of a housing having an inlet and an outlet and a diaphragm adapted to be reciprocated to cause flow of flood through the inlet and the outlet, a brushless dc motor mounted on the housing, the motor having a fixed ball screw nut and a ball screw mounted for axial movement with respect to the motor rotor while being fixed against rotation with respect to the rotor whereby rotation of the rotor causes the screw to move axially with respect to the motor thereby actuating the pump diaphragm.

5 Claims, 3 Drawing Figures

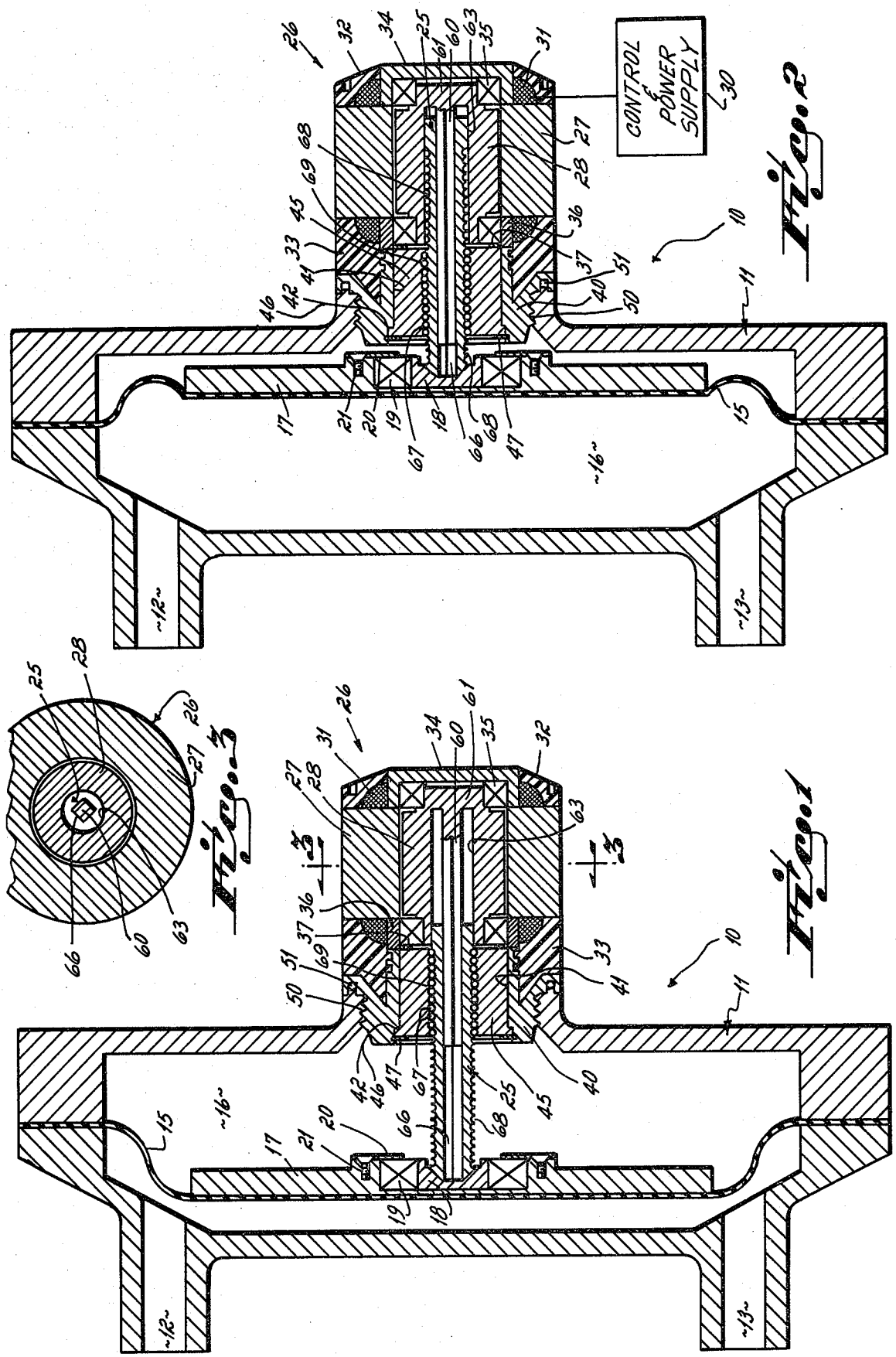

ACTUATOR FOR HEART PUMP

This invention relates to a heart pump, and more particularly, to a left ventricle assist device (LVAD). In a normally functioning heart, it is the left ventricle which performs the major portion of the blood pumping function in that it pumps the blood throughout the body. A failing heart which no longer has the muscular capability of performing the function of pumping blood throughout the body may be kept operative through the use of an LVAD wherein that function of pumping blood throughout the body is taken over by a motor-driven pump.

It has been an objective of the LVAD technology generally to implant a pump and actuator in the body, the pump having an inlet and outlet which are connected directly to the left ventricle of the heart.

One mode of implantation involves the removal of the sixth rib and locating a pancake-shaped pump behind the rib cage with the actuator for the pump projecting between the fifth and seventh ribs. The assembly is covered over by skin of the patient.

The requirements for the pump actuator are obviously severe because of the requirement of pumping approximately 100 beats per minute at a pressure of approximately 120 mm Hg. One form of actuator which is being considered utilizes a brushless dc motor which operates at in excess of 200 rpm—for example, 2880 rpm—and reverses its direction with every stroke of the pump. Such a motor must be reliable for a long period of time without maintenance, for example, two years. It must be very small, very efficient and handle a wide range of load conditions.

Because of the reversing requirements, it is desired to have the lowest inertia possible while having the highest starting torque possible. These objectives are inconsistent, for in order to develop a high torque, a large diameter rotor is required on the one hand, but on the other hand the inertia increases by the fourth power of the radius of rotating members.

An objective of the invention has been to provide an actuator for a heart pump wherein the inertia is minimized without an undue sacrifice in the starting torque.

The objective of the invention is achieved by providing a brushless dc motor having a rotor, a stator and a nut fixed to one end of the stator. A ball screw has one end mounted in the center of the rotor and a projecting portion passing through the fixed nut. The ball screw and rotor have mating surfaces which permit the screw to move axially with respect to the rotor to prevent relative rotational motion between the screw and the rotor.

More particularly, the rotor has, projecting from it, a square shaft. The screw is hollow, having a square bore which mates with the square shaft. The square shaft permits the axial movement of the screw but prevents the relative rotational movement of the screw with respect to the rotor. The square shaft also extends a substantial distance axially from the rotor thereby keeping the screw axially aligned when it is projected from the rotor.

Another objective of the invention has been to provide an actuator for a pump as described above, the actuator being threaded into a pump housing. This combination admits of a relatively simple operation for replacement of an actuator, the operation consisting of an incision large enough to permit the removal and replacement of the motor.

The objectives and features of the invention will become more readily apparent from the following detailed description taken in conjunction with the accompanying drawings in which:

FIG. 1 is a cross-sectional view of the pump and actuator in the systolic position;

FIG. 2 is a view similar to FIG. 1 showing the pump in the diastolic position; and FIG. 3 is a cross-sectional view taken along lines 3—3 of FIG. 1.

The pump indicated at 10 has a housing 11 having an inlet 12 and an outlet 13 which will be directly connected to the left ventricle of the heart. A flexible diaphragm 15 extends across a cavity 16 in the interior of the pump. A plate 17 is secured to the diaphragm and carries a pad 18 mounted to the plate 17 by a thrust bearing 19. The bearing pad 18 is secured to the plate 17 by a washer 20 which overlies the outer race of the bearing 19 and is mounted on the plate 17 by screws 21.

The pad 18 is engaged by a ball screw 25 which is adapted to be reciprocated within the cavity 16 to drive the plate 17 to the left, to the systolic position. Thereafter, the screw 25 is retracted and the natural flow of blood into the pump causes the plate 17 and diaphragm 15 to move to the right to the diastolic position of FIG. 2.

The ball screw 25 is actuated by a brushless direct current motor 26 having a stator 27 and a rotor 28. The motor is energized and controlled by a control system and power supply 30 which is preferably of the type disclosed in U.S. Pat. No. 4,027,215 and application Ser. No. 799,730. The control system utilizes the monitoring of the stator back emf and its zero crossing in order to determine the angular position of the rotor. Thus, there are no external devices required to detect rotor position and which might become fouled by the body fluids. Further, the control system is adapted to count pulses from a zero crossing point or any other selected position and thereby to count the number of revolutions within an accuracy of 1/8th of a revolution. Thus, the operation of the motor including the starting and stopping and reversal of directions can be controlled within a very acceptable accuracy.

The stator has windings 31 which are encased in members 32 and 33 which are of molded plastic. The outside end of the motor is enclosed by a cap 34 which holds bearings 35 by which the rotor 28 is mounted in the stator 27. At the opposite end of the motor, a sleeve 36 and a shim 37 contain bearings 38 supporting the other end.

The plastic 33 holds a sleeve 40 having an internal bore 41 and a shoulder 42. The sleeve 40 receives a ball screw nut 45 which has a shoulder 46 mating with the shoulder 42 to resist movement in a rightward direction as viewed in the drawings. A snap ring 47 positioned in a groove in the sleeve 40 prevents movement of the nut 45 in a leftward direction.

The housing 11 and sleeve 40 have mating threads 50 by which the motor and actuator assembly are secured to the housing 11. An O-ring 51 provides a seal between the housing and the sleeve.

The rotor is hollowed out and has an axially-extending square shaft 60 extending from one end 61 of the rotor out of the rotor to a position adjacent the end of the nut 45. The rotor has a cylindrical surface 63 spaced from the square shaft 60. The ball screw 25 has a square internal surface 66 which mates with the square external surface of the shaft 60 to permit the ball screw to move axially with respect to the rotor 28 but which prevents relative rotary motion between the ball screw and the rotor. A plurality of anti-friction balls 67 interconnect threads 68 of the ball screw with corresponding internal threads 69 of the ball screw nut 45. The nut 45 has provision for a return path for the balls as is customary with ball screw actuators. The motor and actuator assembly have about 1½ inches axial dimension and a diameter of 1.25 inches, thereby permitting the whole pump and actuator unit to be implanted in the body with a minimum of cosmetic problems and psychological and physiological discomfort.

In the operation of the invention, the pump motor, when implanted, is energized. The control circuit 30 causes the motor to operate at about 2880 rpm. After about every fourteen revolutions, the motor reverses, thereby causing the ball screw 25 to project in and out from the rotor 28 thereby causing the diaphragm 15 to reciprocate to effect the pumping action.

Having described my invention, I claim:

1. In a heart pump having a housing, inlet and outlet passageways in said housing, a diaphragm means for reciprocating said diaphragm comprising:
a brushless dc motor mounted on said housing, said motor including a fixed stator and a rotor rotatably mounted in said stator,
a ball screw nut fixed to said stator,
a ball screw engageable with said diaphragm and threadedly connected by anti-friction balls to said nut,
said screw being axially slidable and fixed against rotation with respect to said rotor,
and means for periodically reversing said motor to cause said screw to reciprocate.

2. In a heart pump as in claim 1 further comprising:
a rectangular, axially-extending stem fixed to said rotor,
said screw having a rectangular bore mating with said stem to permit axial sliding movement while preventing relative rotary movement of said screw with respect to said rotor.

3. In a heart pump as in claim 1 further comprising:
a plate mounted on said diaphragm, across said housing,
a pad, a thrust bearing mounting said pad on said plate,
said screw being engageable with said pad.

4. In a heart pump as in claim 1 further comprising:
an end sleeve fixed to said stator and surrounding said nut,
said end sleeve being removably threaded into said housing.

5. In a heart pump as in claim 2,
said stem projecting through said ball screw nut to stabilize said ball screw as it is thrust axially toward said diaphragm.

* * * * *